United States Patent [19]

Hwang

[11] Patent Number: 5,394,492
[45] Date of Patent: Feb. 28, 1995

[54] HIGH POWER SEMICONDUCTOR LASER SYSTEM

[75] Inventor: Cherng J. Hwang, Watchung, N.J.

[73] Assignee: Applied Optronics Corporation, South Plainfield, N.J.

[21] Appl. No.: 156,024

[22] Filed: Nov. 19, 1993

[51] Int. Cl.$^6$ .............................................. G02B 6/32
[52] U.S. Cl. ...................................... 385/33; 385/24; 385/93; 385/118
[58] Field of Search .................. 385/33, 93, 119, 17, 385/24, 34, 37, 43, 89, 121, 115; 372/6, 70, 71

[56] References Cited

U.S. PATENT DOCUMENTS

| | | | |
|---|---|---|---|
| 3,356,854 | 6/1964 | Humphrey | 250/227 |
| 3,590,248 | 6/1971 | Chatterton, Jr. | 250/199 |
| 3,633,035 | 1/1972 | Uchida et al. | 250/199 |
| 3,912,364 | 10/1975 | Hudson | 350/96 |
| 4,186,995 | 2/1980 | Schumacher | 350/96.20 |
| 4,578,791 | 3/1986 | Chen | 372/50 |
| 4,600,267 | 7/1986 | Yamasaki et al. | 350/96.15 |
| 4,662,714 | 5/1987 | Mori | 350/96.20 |
| 4,688,884 | 8/1987 | Scifres et al. | 350/96.15 |
| 4,763,975 | 8/1988 | Scifres et al. | 350/96.15 |
| 4,763,979 | 8/1988 | Heywang | 350/96.20 |
| 4,770,482 | 9/1988 | Sweeney et al. | 385/115 |
| 4,818,062 | 4/1989 | Scifres et al. | 385/33 |
| 4,902,093 | 2/1990 | Bowen | 350/96.20 |
| 4,913,508 | 3/1990 | Blyler et al. | 350/96.16 |
| 4,932,747 | 6/1990 | Russell et al. | 350/96.24 |
| 4,995,687 | 2/1991 | Nagal et al. | 350/96.2 |
| 5,048,911 | 9/1991 | Sang et al. | 385/33 |
| 5,054,018 | 10/1991 | Tremblay | 385/33 |
| 5,058,980 | 10/1991 | Howerton | 385/31 |
| 5,117,473 | 5/1992 | Pan | 385/33 |
| 5,224,193 | 6/1993 | Risk | 385/122 |
| 5,268,978 | 12/1993 | Po et al. | 385/89 X |

OTHER PUBLICATIONS

An Article by NASA'S Jet Propulsion Laboratory, Pasadena, Calif., entitled "Ball Lenses Collimate and Focus Diode-Laser Array Beams", NASA Tech Briefs, Apr. 1993, pp. 26 and 27.

*Primary Examiner*—Rodney B. Bovernick
*Assistant Examiner*—Phan Thi Heartney
*Attorney, Agent, or Firm*—Irwin Ostroff; Erwin W. Pfeifle

[57] ABSTRACT

A high power optical system includes an array of a plurality of semiconductor laser diodes each having a light emitting surface. A plurality of optical fibers each has one end adjacent the light emitting surface of a separate one of the semiconductor laser diodes. A cylindrical lens extends transversely across the one end of each of the optical fibers to direct the light beam from the semiconductor laser diode into the optical fiber. The other ends of the optical fibers are bundled together so as to effectively emit a single beam of a power equal to the combined beams from each of the optical fibers. A delivery optical fiber has an end adjacent the bundled ends of the optical fibers. A lens system, which is between the bundled ends of the optical fibers and the delivery optical fiber, directs the large beam of light emitted from the bundled ends of the optical fibers into the delivery optical fiber. Each of the optical fibers has a numerical aperture less than the numerical aperture of the delivery optical fiber, and preferably a numerical aperture of between about 0.12 and 0.14.

19 Claims, 3 Drawing Sheets

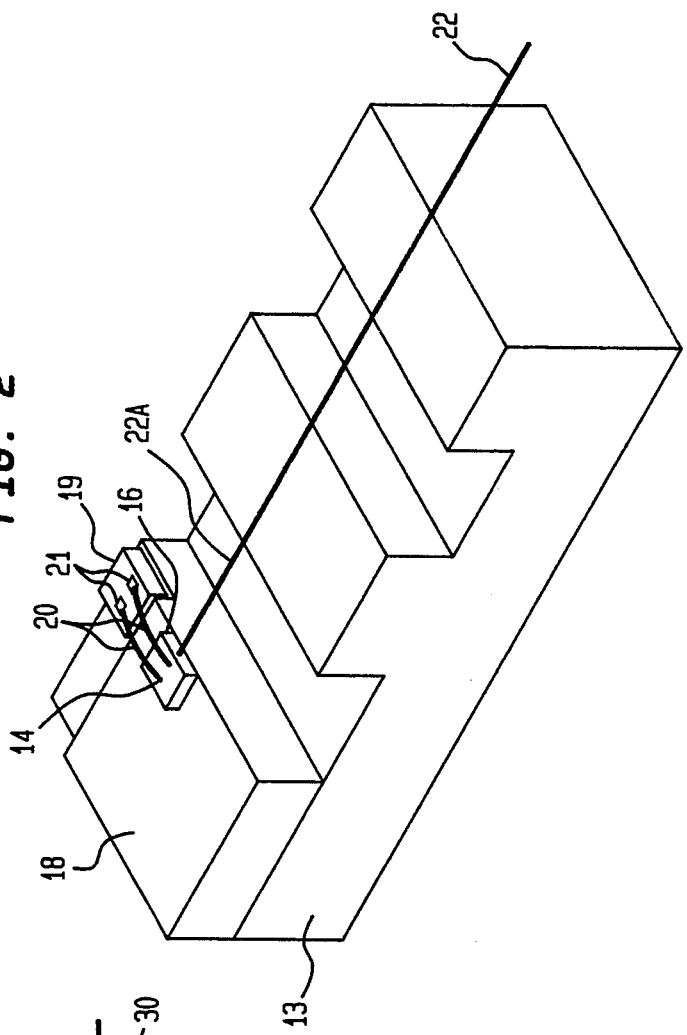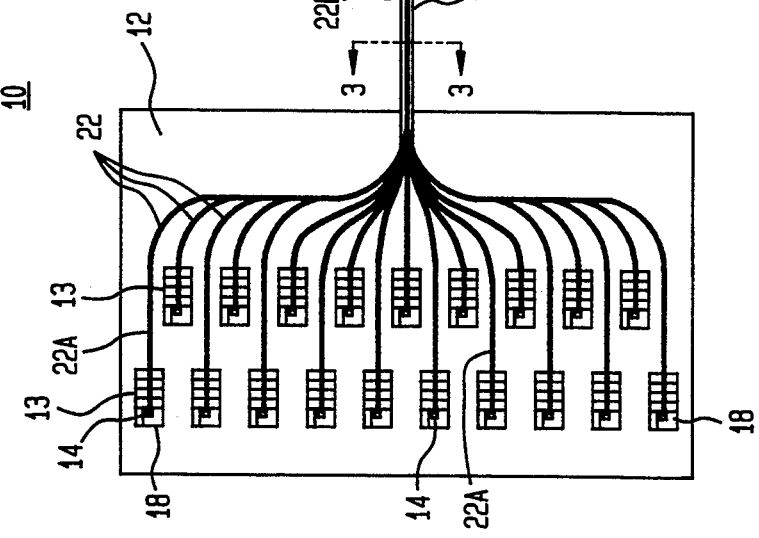

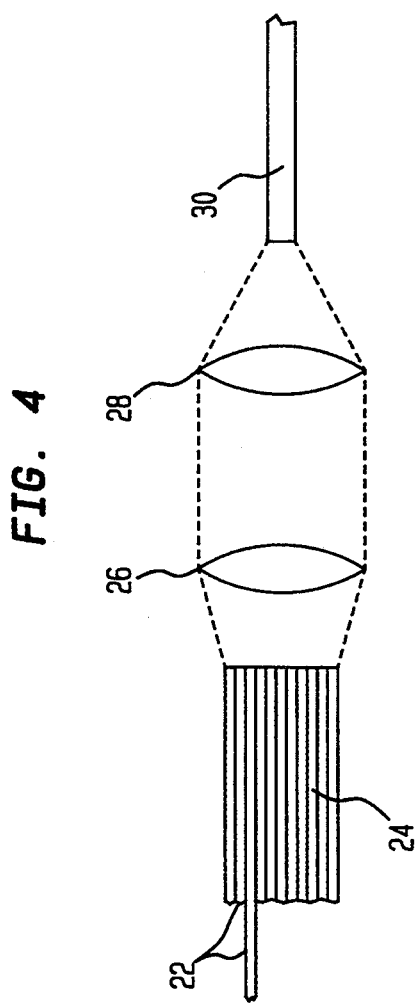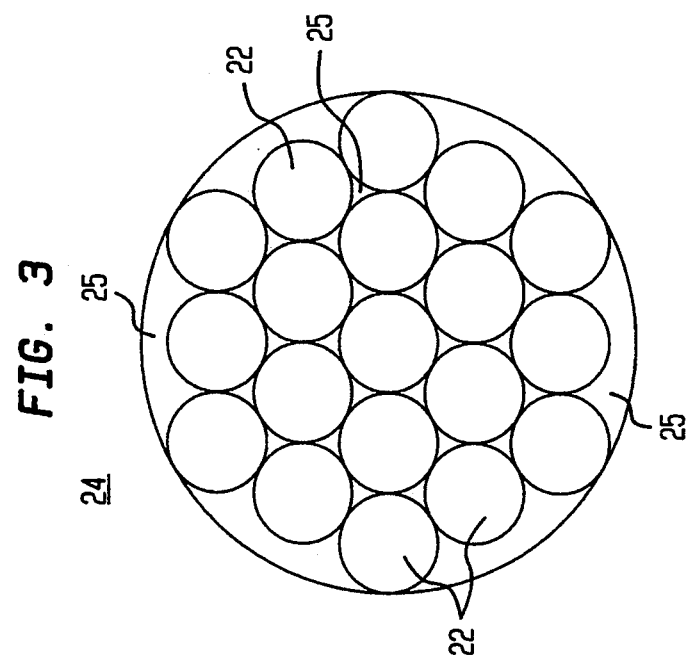

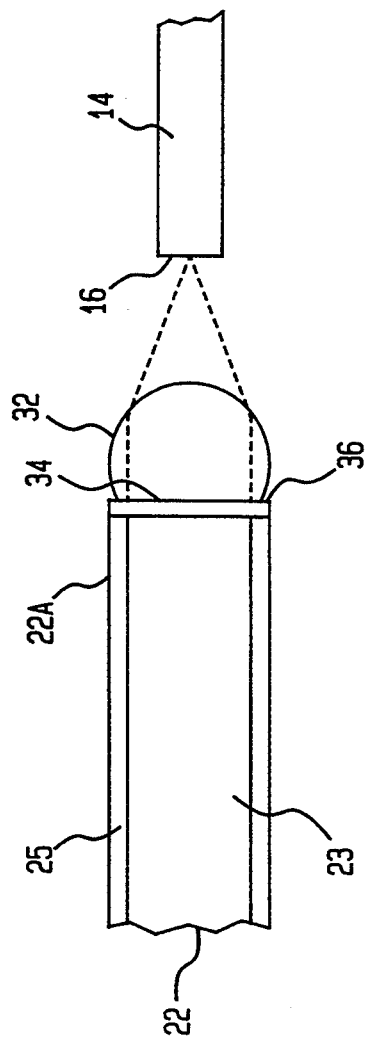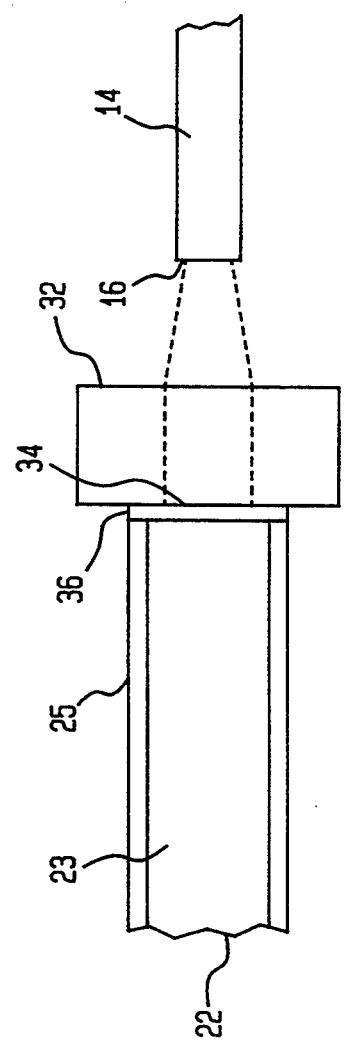

HIGH POWER SEMICONDUCTOR LASER SYSTEM

FIELD OF THE INVENTION

The present invention relates to a high power semiconductor laser system, and, more particularly, to an optical system for achieving the delivery of a high power of light from a plurality of semiconductor lasers to a single optical fiber.

BACKGROUND OF THE INVENTION

Presently, lasers are a common tool for use in many types of medical surgery, such as for eye surgery and the like. To obtain the desired optical power for medical surgery, Nd:YAG and other similar solid-state laser have been used. However, because of the inefficient operation of these solid-state lasers, particularly when pumped by means of flashlamps, such laser systems require water cooling as well as a large power supply. As a result, these lasers are generally not portable and require special wall plug outlets for operation. In addition, these solid-state lasers are also expensive because of their cost and complexity.

Semiconductor lasers, because of their small size, lower cost, and lower power requirements, are very attractive substitutes for Nd:YAG and other similar solid-state lasers. However, a serious problem with semiconductor lasers is that they deliver only relatively low optical power as compared with the solid-state lasers. For example, a broad area semiconductor laser with a 200 micrometer aperture will deliver only about 1 to 2 watts of output power. Therefore, as shown in U.S. Pat. No. 3,590,248 (Chatterton, Jr.), issued Jun. 29, 1971, and entitled "Laser Arrays" a conventional way to achieve more power from semiconductor lasers is to use an array of a plurality of the semiconductor lasers and combine light beams from all of the semiconductor lasers into a single beam through a plurality of optical fibers. Although an array of such semiconductor lasers can deliver as much as several tens of watts, the beam emitted from the semiconductor laser array is not easy to manage. Thus, the beam from the semiconductor laser array is very difficult to focus into a small spot so that it can be coupled into a fiber delivery system, a standard requirement for contact or non-contact surgery.

Means of obtaining high power (several tens of watts) from semiconductor lasers have been a subject of research in the past few years. In an attempt to solve the above problem, it has been suggested that one can work with a highpower semiconductor laser array and develop special fibers with a certain shape to couple as much light as possible from the array. See, for example U.S. Pat. Nos. 4,688,884 (Scifres), issued Aug. 25, 1987, and 4,763,975 (Scifres), issued Aug. 25, 1988. Spectra Diode Labs (SDL) uses a proprietary fiber that, purportedly, can couple about 10 watts from an array into a 400 micrometer core fiber with a 0.4 numerical aperture (NA). The SDL approach, although compact, has major drawbacks. At 10 watts the power is too low for most surgical application, and the NA=0.4 is too high to effectively couple the 10 watts of power into the fiber delivery system which has a standard NA of 0.37. In addition, because a large amount of heat is generated in a small area, water cooling is generally required. The SDL system is therefore not useful in some medical applications.

A different approach has been taken by Laser Diode Inc. Its LDP 4000 delivers 10 watts from a fiber bundle of 2 mm. The LDP 4000 uses 64 semiconductor lasers divided into 16 groups. Each semiconductor laser is coupled to a fiber and therefore 64 fibers are involved in the bundle. Since the standard medical fiber delivery system uses a fiber with a core diameter of equal to or less than 600 micrometers, such system apparently is not useful for medical applications. Furthermore, the system appears to have poor coupling efficiency for each individual semiconductor laser because of the large number of lasers used in the array. As a result, the LDP 4000 is not only inefficient but also is not suitable for some surgical applications.

It is also important to point out that the semiconductor lasers used by both SDL and LDI are all semiconductor lasers with emission wavelengths around 800 nm. Also, the laser arrays mentioned above are vulnerable to failure of the entire system when a single semiconductor laser element fails by exhibiting low resistance.

Efficient coupling of light from a semiconductor laser into an optical fiber has been a subject of interest for many years. This is because of the fact that the emission angles from a semiconductor diode, a PN junction, laser are not symmetrical in both the vertical (perpendicular to the PN junction of the diode laser) and horizontal (parallel to the PN junction) directions. The vertical angle of emission is generally quite large (approximately 40 degrees FWHM) compared with the horizontal angle of emission (approximately 8 degrees FWHM). This makes the coupling efficiency to a typical fiber (with a NA approximately 0.2) quite small. Efforts to increase coupling efficiency include changing the waveguide structure of the semiconductor laser, using external optics and shaping the fiber tip. Changing the waveguide structure can improve the emission angle somewhat, but always involves compromises of other operating characteristics. Using external optics involves the use of very high NA (greater than 0.5) collecting lenses (collimating lenses), and then refocusing the light into the fiber by the use of another lens (See "Ball Lenses Collimate, etc" NASA Tech Briefs, April, 1993, pp. 26–27, U.S. Pat. No. 4,995,687 (Nagal et al.), issued Feb. 26, 1991, and U.S. Pat. No. 4,186,995 (Schumacher), issued Feb. 5, 1980).

High coupling efficiency can be achieved by the use of lenses with small emitting aperture lasers, such as the lower power semiconductor lasers used in the communication, compact disc players and laser printers. However, such lenses are not useful for high power lasers with wide emitting aperture because the high NA of the lenses tends to focus the light in the horizontal direction, causing such to enter into the fiber with a larger angle than the acceptance angle of the fiber. Shaping the fiber tip has the same effect as the use of external optics but does not require sophisticated mounting mechanism for the lenses. Therefore, some other method must be derived to increase the coupling efficiency of high power broad area semiconductor lasers into optical fibers.

As is well known, all the high power semiconductor lasers comprise a structure with a wide aperture (or stripe). This wide aperture can be formed by one stripe or consist of many small stripes filling such aperture. In either case, the transverse mode in the direction of the stripes is multimode in nature and the nearer field (light distribution of the emitting facet of the semiconductor laser) is filamentary in nature (many bright spots that lase simultaneously). The light emission pattern (far field) is generally quite complicated and dependent on the input current. Direct use of such beam patterns for imaging or focusing (without using an optical lens imaging system) is not desirable. Furthermore, such broad semiconductor lasers also exhibit large astigmatism making the use of a conventional optical lens impractical. As a result, it is desirable to alter the beam characteristics before the introduction of an optics.

SUMMARY OF THE INVENTION

The present invention is directed to an optical system which comprises a plurality of light sources (e.g., semiconductor laser diodes) each adapted to emit a beam of light from a surface thereof. A plurality of first optical fibers, each has one end thereof adjacent the light emitting surface of a separate one of the light sources so as to receive the beam of light emitted therefrom. The other ends of the first optical fibers are bundled together in closely spaced relation so as to effectively emit a single beam of light which is a combination of the beams from all of the first optical fibers. A second optical fiber has an end adjacent the other ends of the first optical fibers to receive the beam of light emitted from the bundle of first optical fibers. Means are provided for directing the beam of light from the bundled other ends of the first optical fibers into the second optical fiber. The first optical fiber has a numerical aperture less than that of the second fiber.

The invention will be better understood from the following more detailed description taken with the accompanying claims and drawings.

BRIEF DESCRIPTION OF THE DRAWINGS

FIG. 1 is a schematic view of a high power semiconductor laser system in accordance with the present invention;

FIG. 2 is a perspective view of one semiconductor laser diode and optical fiber which can be used in the system of the present invention;

FIG. 3 is a sectional view of the bundle of optical fibers taken along line 3—3 of FIG. 1;

FIG. 4 is an enlarge schematic view of the optical focusing arrangement between the bundle of optical fibers and the delivery fiber of the system of the present invention;

FIG. 5 is a schematic side view showing optical coupling between a semiconductor laser diode and an optical fiber; and FIG. 6 is a top schematic side of the optical coupling between the semiconductor laser diode and an optical fiber.

The drawings are not necessarily to scale.

DETAILED DESCRIPTION

Referring initially to FIG. 1, there is shown a schematic view of a high power semiconductor laser system 10 in accordance with the present invention. Laser system 10 comprises a support 12 having thereon a plurality of light emitting devices 14, such as semiconductor laser diodes, which are capable of emitting beams of light, a plurality of separate optical fibers 22, lenses 26 and 28 and a delivery optical fiber 30. As shown, the semiconductor laser diodes 14 are arranged in two rows with the semiconductor laser diodes 14 in one row being between the semiconductor laser diodes 14 in the other row. Each semiconductor laser diode 14 is mounted on a heat conductive base 18 which is mounted on a fiber pigtail shelf (submount assembly) 13 that is mounted on the support 12. Each of the plurality of separate optical fibers 22 has one end 22a thereof positioned adjacent a separate semiconductor laser diode 14 so as to receive the beam of light emitted from the associated semiconductor laser diode 14. Other ends 22b of each of the optical fibers 22 are secured together in closely spaced relation to form a bundle 24 of the optical fibers 22. The delivery optical fiber 30, which is a single optical fiber, has an end 30a adjacent the end of the bundle 24 of the optical fibers 22 so as to receive the combined beam of light from the bundle 24.

Referring now to FIG. 2, there is shown an enlarged perspective more detailed view of a portion of system 10 of FIG. 1 comprising one of the semiconductor laser diodes 14 and its associated optical fiber 22. The semiconductor laser diode 14 is a chip which is mounted on a heat conducting base 18. The base 18 is mounted on the submount assembly 13. A separate ceramic pad (an electrical insulator) 19, which has separate bonding (conductive) pads 21 on a surface thereof, is mounted on each base 18. A pair of separate electrical leads 20 couple each laser diode 14 to pads 21 of one of the bases 18. A power supply (not shown) is coupled to all of the pads 21 so as to supply power to each laser diode 14. In a preferred embodiment, base 18 and submount assembly are copper and support 12 is aluminum.

The semiconductor laser diode 14 has an end surface 16 from which a light beam is emitted. The semiconductor laser diode 14 may be a GaInAs/GaAs strained-layer laser diode which emits light at a nominal wavelength of 980 nm. However, other well known types of semiconductor laser diodes 14 which emit in the wavelength range from visible to mid-infrared can be used. However, the strained GaInAs semiconductor laser diodes have higher catastrophic damage threshold, high operating temperature and hence better reliability. Also, such semiconductor laser diodes have a wavelength very close to the wavelength of Nd:YAG solid state lasers. The semiconductor laser diode 14 has an emitting aperture at its emitting surface 16 of about 150–200 micrometers.

A single optical fiber 22 is mounted on the support 12 with the one end 22a being adjacent and aligned with the light emitting surface 16 of the semiconductor laser diode 14. Optical fiber 22 is of a composition to have a low numerical aperture (NA), between about 0.12 and 0.14.

Referring to now FIGS. 5 and 6, there are shown a side view and top view, respectively, of a coupling between a semiconductor laser diode 14 and an optical fiber 22. The optical fiber 22 has a core 23 covered with a cladding 25. The optical fiber 22 may be a silica core 23 having a diameter of about 200 micrometers covered with a silica cladding 25 having a diameter of about 240 micrometers. The optical coupling comprises a cylindrical lens 32 having a diameter about the same as the diameter of the optical fiber 22. Lens 32 can be a standard drawn glass fiber or rod with a high index of refraction and a NA higher than that of the optical fiber 22. Lens 32 extends transversely across the end 22a of the optical fiber 22 and has a flat 34 which is seated flush against the end surface of the first end 22a of the optical fiber 22. The lens 32 is secured to the end 22A of the optical fiber 22 by means of a thin layer 36 of a suitable cement, such as a clear epoxy which has an index of refraction between those of the lens 32 and the optical fiber 22. The lens 32 substantially collimates in the vertical direction the light emitted from the light emitting surface 16 of the semiconductor laser diode 14 and guides the light through the cement layer 36 into the optical fiber 22. The lens 32 has no effect on the light emission in the horizontal direction. However, since the emission angle in the horizontal direction is small compared to the collection angle of optical fiber 22, light in the horizontal direction is largely coupled into the fiber 22.

The lens 32 is positioned at a predetermined distance from the semiconductor laser diode 14 so that as much light as possible from the semiconductor laser diode 14 is coupled into the fiber 22. Since the index of refraction of the lens 32 is large, the lens 32 is positioned very close to the semiconductor laser diode 14 (typically about 25 micrometers), and the spot size in the collimated direction is small (e.g., about 1 micrometer). Thus, most of the light beam emitted from the semiconductor laser diode 14 in the vertical direction is coupled into the core of the optical fiber 22.

Referring to now FIG. 3, there is shown a cross-sectional view of the bundle 24 of the optical fibers 22 of FIG. 1. The optical fibers are arranged in contacting relationship and are secured together by a suitable cement 25 to form the bundle 24. The number of optical fibers 22 in the bundle 24 can be any suitable number. However, maximum power is delivered through the smallest area when 7, 19, 31, 37, etc. of the optical fibers 22 are used.

Referring now to FIG. 4, there is shown a schematic view of the optical coupling of the bundle 24 of the optical fibers 22 to the delivery optical fiber 30. The beam of light emitted from the ends of the bundle 24 is relatively large and is reduced in size to be received by the delivery optical fiber 30 by means of a beam reduction optical arrangement comprising a pair of lenses 26 and 28. The lenses 26 and 28 are arranged between the end of the bundle 24 and an end 30a of the delivery optical fiber 30 with the lens 26 being adjacent the end of the bundle 24 and the lens 28 being adjacent the end 30a of the delivery optical fiber 30. The lens 26 is designed to collimate the light beam emitted from the end of the bundle 24 and the lens 28 is designed to receive the collimated beam of light and reduce the light beam to a spot size substantially equal to the diameter of the delivery optical fiber 30. The delivery optical fiber 30 can be part of a standard fiber delivery system for medical surgery applications, and therefore, generally has a core diameter that is smaller than the cross-sectional area of bundle 24.

In general, to avoid loss of light coupled to the delivery optical fiber 30, the NA of the delivery optical fiber 30 is chosen to be equal to or greater than the NA of the lens 28, and the NA of the individual fibers 22 of the bundle 24 is chosen to be equal to or less than the NA of the lens 26. Assuming the need to reduce the spot size by a factor of "a", then the numerical aperture (NA) of lens 26 should be equal to the NA of lens 28 divided by "a". In other words, NA (lens 26) = (i/a) NA (lens 28)

In practical cases, the NA of the delivery optical fiber 30 is fixed by the fiber delivery system. For example, in contact surgery, such NA is typically equal to 0.37. The NA of the optical fibers 22 forming the bundle 24 must then be $(1/a) \times 0.37$. From this requirement, an appropriate optical fiber 22 for the bundle 24 as well as the number of optical fibers (and therefore semiconductor laser diodes 14) can be chosen. As previously stated, 7, 19, 31, 37, etc. of the optical fibers 22 can be packaged with maximum filling factor to form the bundle 24. If each optical fiber 22 has a core diameter of 200 micrometers with a cladding diameter of 240 micrometers, the bundle 24 will have a diameter of approximately 1.510 mm for a 31 fiber arrangement. A beam reduction of a factor of 2.7 is then required to couple the light into a 600 micrometer core delivery optical fiber 30. Thus, the NA of the individual optical fibers 22 forming the bundle should be $(1/2.7) \times 0.37 = 0.137$. A system having 31 optical fibers 22 and the beam reduction optics described above can couple 25 watts of optical power into a 600 micrometer, 0.37 NA delivery fiber 30. One of the 31 optical fibers 22 may be used for a visible semiconductor laser diode 14 for aiming purposes.

Thus, there is provided by the present invention an optical delivery system 10 in which a plurality of semiconductor laser diodes 14 emit individual beams of light into separate optical fibers 22. The optical fibers 22 are formed into a bundle 24 which emits a high power beam of light equal to the combined beams of light from all of the semiconductor laser diodes 14. The high power beam of light is directed into a single delivery fiber 30 which delivers the high power beam of light to a desired use, such as for medical surgery. High efficiency optical couplings are provided between each semiconductor laser diode 14 and its respective optical fiber 22 and between the bundle 24 of the optical fibers 22 and the delivery fiber 30 to transfer an optimum about of the light along the system 10. Also, the optical fibers 22 have a numerical aperture (NA) less than that of the delivery fiber 30 so as to be able to transmit the high power of light. Medical surgery systems made in accordance with the system 10 of the present invention have produced overall coupling efficiencies of 80% compared to about 50% for conventional system of generally the same type. Also, each of the semiconductor laser diodes 14 operates independently of the others so that if one of the semiconductor laser diodes 14 fails, it can be replaced without effecting the operation of the others or the substantial continued operation of the system 10. In addition, each semiconductor laser diode 14 is spaced from the other sufficiently so that its heat is dissipated through its heat conducting base 18 to the support 12 without causing heating problems for the other semiconductor laser diodes 14.

It is to be appreciated and understood that the specific embodiments of the invention are merely illustrative of the general principles of the invention. Various modifications may be made consistent with the principles set forth. For example, as previously indicated various types of known semiconductor laser diodes can be used. Also, optical fibers of various materials can be used as long as they have the appropriate numerical aperture.

What is claimed is:

1. An optical system for generating an output light beam usable in medical laser intervention comprising:
   a plurality of light sources, each light source operating independently of the other light sources and adapted to emit a separate beam of light from a surface thereof, at least one of the plurality of light sources selectively generating a light beam having a wavelength within a visible light spectrum for use in visibly aiming the output light beam of the optical system, and the remaining light sources of the plurality of light sources selectively generating light beams having wavelengths within a predetermined range of wavelengths which are useful in medical laser intervention;

a plurality of first optical fibers, each of said first optical fibers having one end coupled to the surface of a separate one of the plurality of light sources so as to receive the beam of light emitted therefrom, the other ends of the first optical fibers being bundled together in close relation so as to effectively emit a single beam of light which is a combination of the beams from all of the first optical fibers;

a second optical fiber having an end positioned relative to the other ends of the first optical fibers to receive the beam of light emitted from the bundle of the first optical fibers and deliver the beam of light as the output light beam of the optical system without further processing;

means for directing the beam of light from the bundled other ends of the first optical fibers into the second optical fiber; and the first optical fibers having a numerical aperture less than that of the second optical fiber.

2. The optical system of claim 1 in which the first optical fibers have a numerical aperture of between about 0.12 and 0.14.

3. The optical system of claim 2 in which each of the light sources is a semiconductor laser diode.

4. The optical system of claim 3 further comprising separate optical means between the light emitting surface of each of the laser diodes and the one end of its respective first optical fiber to direct the beam of light from the laser diode into the first optical fiber.

5. The optical system of claim 4 in which the separate optical means comprises a separate cylindrical lens extending transversely across the end of the first optical fiber and having a flat surface seated against the end of the first optical fiber.

6. The optical system of claim 5 further comprising means for bonding the cylindrical lens to its respective first optical fiber.

7. The optical system of claim 6 in which the bonding means is a layer of a cement between the flat surface of the cylindrical lens and the end of the first optical fiber.

8. The optical system of claim 7 in which the bonding means is a layer of a clear epoxy having an index of refraction between the indices of refraction of the cylindrical lens and the one optical fiber.

9. The optical system of claim 8 in which the numerical aperture of the cylindrical lens is greater than the numerical aperture of the first optical fiber.

10. The optical system of claim 1 in which the means for directing the beam of light from the bundled other ends of the first optical fibers into the second optical fiber comprises a system of lenses.

11. The optical system of claim 10 in which the system of lenses comprises first and second lenses between the bundled end of the first optical fibers and the second optical fiber.

12. The optical system of claim 11 in which the first lens is adjacent the bundled end of the first optical fibers and adapted to collimate the beam of light emitted from the bundled end of the first optical fibers, and the second lens is adapted to receive the collimated light from the first lens and to reduce the beam of light to a diameter substantially equal to the diameter of the second optical fiber.

13. The optical system of claim 12 in which the first lens has a numerical aperture equal to or greater than that of the first optical fibers, and the second lens has a numerical aperture equal to or less than that of the second optical fiber.

14. An optical system for generating an output light beam usable in medical laser intervention comprising:

a plurality of semiconductor laser diodes arranged in an array and having light emitting surfaces facing in a same direction, each laser diode operating independently of the other laser diodes and at least one of the plurality of laser diodes selectively generating a light beam having a wavelength within a visible light spectrum for use in visibly aiming the output light beam of the optical system, and the remaining laser diodes of the plurality of laser diodes selectively generating light beams having wavelengths within a predetermined range of wavelengths which are useful in medical laser intervention;

a plurality of first optical fibers, each of said first optical fibers having one end coupled to the light emitting surface of a separate one of the plurality of semiconductor laser diodes so as to receive a beam of light emitted therefrom, the other ends of the first optical fibers being bundled together in close relation so as to effectively emit a single beam of light which is a combination of the beams from all of the first optical fibers;

means between the light emitting surface of each of the semiconductor laser diodes and its adjacent first optical fiber for directing the light beam from the semiconductor laser diode into the one end of the first optical fiber;

a second optical fiber having an end positioned relative to the other ends of the first optical fibers to receive the beam of light emitted from the bundle of the first optical fibers and to deliver the beam of light as the output light beam of the optical system without further processing;

means for directing the beam of light from the bundled other ends of the first optical fibers into the second optical fiber; and the first optical fibers having a numerical aperture less than that of the second optical fiber.

15. The optical system of claim 14 in which the first optical fibers have a numerical aperture of between about 0.12 and 0.14.

16. The optical system of claim 15 in which the means for directing the beam of light from each semiconductor laser diode into it adjacent first optical fiber comprises a separate cylindrical lens extending transversely across the end of the first optical fiber and having a flat surface seated against the end of the first optical fiber.

17. The optical system of claim 16 including a clear epoxy resin between the flat surface of the cylindrical lens and the end of the first optical fiber to secure the cylindrical lens to the first optical fiber.

18. The optical system of claim 17 in which the means for directing the beam of light from the bundle of the first optical fibers into the second optical fiber comprises a pair of lenses between the bundles ends of the first optical fibers and the second optical fiber.

19. The optical system of claim 18 in which one of the pair of lenses is adjacent the bundled ends of the first optical fibers and is adapted to collimate the beam of light emitted from the bundled ends of the first optical fibers, and the other of the pair of lenses is adjacent the second optical fiber and is adapted to receive the collimated beam of light from the first lens and reduce the beam to a diameter substantially equal to the diameter of the second optical fiber.

* * * * *